United States Patent
Koh

(10) Patent No.: US 11,559,677 B2
(45) Date of Patent: Jan. 24, 2023

(54) TUBE CONNECTOR FOR MEDICAL TREATMENT

(71) Applicant: Jung Seo Koh, Seoul (KR)

(72) Inventor: Jung Seo Koh, Seoul (KR)

( * ) Notice: Subject to any disclaimer, the term of this patent is extended or adjusted under 35 U.S.C. 154(b) by 303 days.

(21) Appl. No.: 16/894,930

(22) Filed: Jun. 8, 2020

(65) Prior Publication Data

US 2020/0384257 A1    Dec. 10, 2020

(30) Foreign Application Priority Data

Jun. 10, 2019    (KR) .......................... 10-2019-0068094

(51) Int. Cl.
| A61M 39/10 | (2006.01) |
| A61M 39/24 | (2006.01) |
| A61M 5/168 | (2006.01) |

(52) U.S. Cl.
CPC ...... *A61M 39/105* (2013.01); *A61M 5/16813* (2013.01); *A61M 39/24* (2013.01); *A61M 5/16881* (2013.01); *A61M 2039/2486* (2013.01); *A61M 2205/75* (2013.01)

(58) Field of Classification Search
CPC ................ A61M 39/105; A61M 39/24; A61M 5/16813; A61M 5/16881; A61M 2039/2486; A61M 2205/75
See application file for complete search history.

(56) References Cited

U.S. PATENT DOCUMENTS

| 3,730,224 | A | * | 5/1973 | Prisk | F16K 27/02 |
| | | | | | 137/625.33 |
| 4,526,473 | A | * | 7/1985 | Zahn, III | G04B 47/00 |
| | | | | | 968/398 |
| 5,186,714 | A | * | 2/1993 | Boudreault | A61M 1/774 |
| | | | | | 606/49 |
| 5,618,268 | A | * | 4/1997 | Raines | A61M 39/26 |
| | | | | | 604/82 |
| 7,766,044 | B2 | * | 8/2010 | Makowan | F16K 15/147 |
| | | | | | 137/859 |
| 2007/0129692 | A1 | * | 6/2007 | Enomoto | A61M 39/24 |
| | | | | | 604/284 |
| 2008/0291667 | A1 | * | 11/2008 | Bushee | F41B 15/08 |
| | | | | | 362/206 |

(Continued)

FOREIGN PATENT DOCUMENTS

| KR | 10-1931795 | 12/2018 |
| KR | 10-2019-0068094 | 6/2019 |

*Primary Examiner* — Patrick C Williams
(74) *Attorney, Agent, or Firm* — Fay Sharpe LLP

(57) ABSTRACT

Disclosed is a tube connector for medical treatment including a housing including an internal channel configured to allow an inflow pipe disposed at the front end thereof and an outflow pipe disposed at the rear end thereof to fluidly communicate with each other, an insertion hole formed from the outer surface of the rear end of the housing to the internal channel, and at least one branch pipe disposed so as to fluidly communicate with the internal channel, a push button having a through hole, the push button being disposed in the insertion hole so as to be movable upwards and downwards, and an elastically deformable dome-shaped balloon configured to surround the insertion hole of the housing, the lower part of the balloon being open, wherein the internal channel of the housing is opened and closed through the upward and downward movement of the push button.

5 Claims, 5 Drawing Sheets

(56) References Cited

U.S. PATENT DOCUMENTS

| | | | | |
|---|---|---|---|---|
| 2010/0249723 A1* | 9/2010 | Fangrow, Jr. | ............ | A61M 39/1011 604/247 |
| 2011/0056569 A1* | 3/2011 | Chambo | ............... | F16K 15/147 137/843 |
| 2015/0018780 A1* | 1/2015 | Butterfield | ............ | A61M 39/24 604/246 |
| 2015/0352349 A1* | 12/2015 | Carmody | .............. | A61M 39/24 137/544 |

\* cited by examiner

TUBE CONNECTOR FOR MEDICAL TREATMENT

CROSS REFERENCE TO RELATED APPLICATION

The present application claims priority to Korean Patent Application No. 10-2019-0068094, filed Jun. 10, 2019, the entire contents of which is incorporated herein for all purposes by this reference.

BACKGROUND OF THE INVENTION

Field of the Invention

The present invention relates to a tube connector for medical treatment, and more particularly to a connector configured to allow a plurality of intravenous fluid vessels to be connected thereto in an intravenous fluid infusion set for medical treatment configured to inject an intravenous fluid into the body of a patient.

Description of the Related Art

In general, an intravenous fluid infusion set for medical treatment, which is a tool used to inject a fluid (or a medicinal fluid, an intravenous fluid, blood, etc.) stored in an intravenous fluid vessel into the body of a patient, includes an intravenous fluid vessel, a syringe inserted into a vein of the patient in order to inject an intravenous fluid into the vein, and an intravenous fluid supply tube interposed between the intravenous fluid vessel and the syringe, the intravenous fluid supply tube being configured to define the movement path of the intravenous fluid.

In a conventional intravenous fluid infusion set, at least one three-way valve is installed to an intravenous fluid supply tube in order to supply various kinds of intravenous fluids stored in a plurality of intravenous fluid vessels to a patient individually or after being mixed (see FIG. 7 of Patent Document 1). For reference, the three-way valve may be a three-way stopcock, which may be purchased on the market.

In the conventional intravenous fluid infusion set, functional construction members configured to prevent backward flow of an intravenous fluid, to filter foreign matter/air, and to control the flow rate of the intravenous fluid may be mounted to the intravenous fluid supply tube as needed. Since various construction members are mounted to the intravenous fluid supply tube in the conventional intravenous fluid infusion set, as described above, the number of coupling regions between the respective construction members inevitably increases. In the case in which any one of the construction members is unexpectedly separated from the intravenous fluid supply tube, an intravenous fluid that is supplied to the patient is discharged to the outside, and foreign matter (blood) spouts from the body of the patient, contaminating the surroundings. In addition, contamination due to contact with the outside occurs.

RELATED ART DOCUMENTS

Patent Documents (Patent Document 1) Korean Registered Patent Publication No. 10-1931795

SUMMARY OF THE INVENTION

The present invention has been made in view of the above problems, and it is an object of the present invention to provide a tube connector for medical treatment capable of stably transferring an intravenous fluid that is individually supplied from at least one intravenous fluid vessel and of effectively controlling the flow of the intravenous fluid as needed.

In accordance with the present invention, the above and other objects can be accomplished by the provision of a tube connector for medical treatment including a housing, a push button, and a balloon, wherein an internal channel of the housing is opened and closed through upward and downward movement of the push button.

To this end, the housing may include an internal channel configured to define the movement path of an intravenous fluid, an inflow pipe formed at the front end of the housing so as to fluidly communicate with the internal channel, an outflow pipe disposed at the rear end of the housing so as to fluidly communicate with the internal channel, an insertion hole formed from the outer surface of the rear end of the housing to the internal channel, a reception recess formed from the inner circumferential surface of the internal channel in the thickness direction of the housing so as to be opposite the insertion hole, and at least one branch pipe disposed at the outer surface of the front end of the housing so as to fluidly communicate with the internal channel. The push button may include a length portion having a through hole formed therethrough and an extension portion located at the upper end of the length portion so as to be disposed at the outer surface of the housing, wherein the push button may be disposed in the insertion hole so as to be movable upwards and downwards. The balloon may be formed in an elastically deformable dome shape so as to surround the insertion hole of the housing, and the lower part of the balloon may be open.

In an embodiment of the present invention, a check valve may be disposed in the internal channel or the branch pipe of the housing, and a filter may be disposed in the internal channel or the branch pipe.

The check valve may include a ring-shaped frame disposed around the inner circumferential surface of the internal channel or the branch pipe and a plurality of segment panels disposed around the ring-shaped frame in a dome shape, wherein the plurality of segment panels may be formed in a curved triangular shape that is convex toward the downstream side and the sides of the segment panels may be disposed so as to overlap each other.

In the present invention, the through hole may have a sectional shape that is wide at the front thereof and is narrow at the rear thereof.

In the present invention, at least one coupling recess may be provided in the inner surface of the insertion hole of the housing in the upward-downward movement direction of the push button, and a coupling protrusion may be provided on the outer surface of the length portion so as to correspond to the coupling recess.

Also, in the present invention, a direction indicator configured to indicate the movement direction of the intravenous fluid may be provided at the downstream side outer surface of the housing adjacent to the outflow pipe.

The features and advantages of the present invention will be more clearly understood from the following detailed description taken in conjunction with the accompanying drawings.

It should be understood that the terms used in the specification and appended claims should not be construed as being limited to general and dictionary meanings, but should be construed based on meanings and concepts according to the spirit of the present invention on the basis of the principle that the inventor is permitted to define appropriate terms for the best explanation.

BRIEF DESCRIPTION OF THE DRAWINGS

The above and other objects, features and other advantages of the present invention will be more clearly understood from the following detailed description taken in conjunction with the accompanying drawings, in which:

FIG. 3 is a partial cutaway view of the tube connector for medical treatment shown in

FIG. 2;

DETAILED DESCRIPTION OF THE INVENTION

Figure 1:
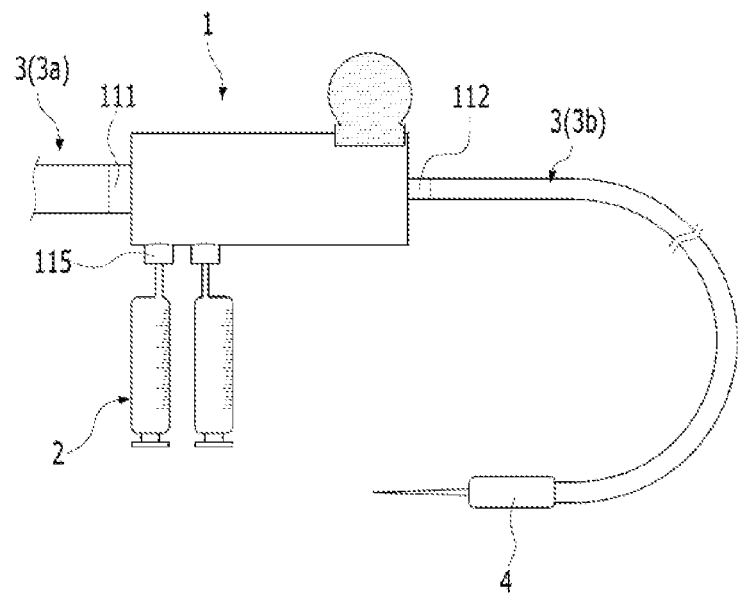
FIG. 1 is a view showing the construction of an intravenous fluid infusion set adopting a tube connector for medical treatment according to the present invention.

Objects, specific advantages, and novel features of the present invention will be apparent from exemplary embodiments and the following detailed description in connection with the accompanying drawings. It should be noted that, when reference numerals are assigned to the elements of the drawings, the same reference numeral is assigned to the same elements even when they are illustrated in different drawings. Also, in the following description of the present invention, a detailed description of known functions and configurations incorporated herein will be omitted when the same may obscure the subject matter of the present invention. In this specification, the terms "first", "second", etc. are used to distinguish one element from another, and elements are not limited by the terms. In the accompanying drawings, some elements are exaggerated, omitted, or schematically illustrated, and the size of each element does not entirely reflect the actual size thereof.

Hereinafter, embodiments of the present invention will be described in detail with reference to the accompanying drawings.

As shown in FIG. 1, a tube connector 1 for medical treatment according to a preferred embodiment of the present invention is a construction member that is adopted in an intravenous fluid infusion set for medical treatment configured to guide an intravenous fluid (and/or a medicinal fluid) stored in an intravenous fluid vessel 2 into the body of a patient and to control a movement path of the intravenous fluid that is guided along an intravenous fluid supply tube 3.

In brief, the intravenous fluid infusion set for medical treatment may include an intravenous fluid vessel configured to store an intravenous fluid, an intravenous fluid supply tube 3 (3a and 3b) fluidly communicating with the intravenous fluid vessel, the intravenous fluid supply tube extending long, an injection port 4 configured to inject the intravenous fluid transferred along the intravenous fluid supply tube into the body of a patient, e.g. into a vein of the patient, and a connector 1 interposed between the intravenous fluid supply tube 3b and the intravenous fluid vessel, the connector being configured to limit the movement of the intravenous fluid.

In the intravenous fluid infusion set for medical treatment, the upstream side intravenous fluid supply tube 3a, which is configured to discharge the intravenous fluid stored in the intravenous fluid vessel, and the downstream side intravenous fluid supply tube 3b, which is configured to supply the intravenous fluid to the injection port 4 configured to be inserted into the vein of the patient, are coupled to each other via the connector 1 in the longitudinal direction so as to communicate with each other, wherein the upstream side intravenous fluid supply tube 3a is disposed between one end of the connector 1 and the intravenous fluid vessel 2 so as to fluidly communicate therewith and the downstream side intravenous fluid supply tube 3b is disposed between the other end of the connector 1 and the injection port 4 so as to fluidly communicate therewith.

In addition, the connector 1 may supply a combination of various kinds of intravenous fluids to the patient through at least one branch pipe 115 disposed adjacent to one end thereof.

FIG. 1 schematically shows an intravenous fluid infusion set for medical treatment including the tube connector 1 for medical treatment according to the present invention. However, the present invention is not limited thereto. The intravenous fluid infusion set may be differently constructed depending on the purpose of use. Here, the intravenous fluid vessel 2 may be an intravenous fluid bag (not shown) configured to store an intravenous fluid and to supply the intravenous fluid to the patient or a syringe, as shown. That is, the tube connector 1 for medical treatment is connected to the upstream side intravenous fluid supply tube 3a via an inflow pipe 111 so as to fluidly communicate therewith. However, the present invention is not limited thereto. A syringe may be directly connected to the tube connector 1 for medical treatment in order to supply an intravenous fluid. Correspondingly, intravenous fluid supply tubes may be connected to at least one branch pipe 115 of the tube connector 1 for medical treatment, instead of syringes, in order to supply an intravenous fluid. In addition, the injection port may be a needle configured to inject an intravenous fluid into a vein, i.e. a catheter, as is well known by those skilled in the art.

Figure 2:
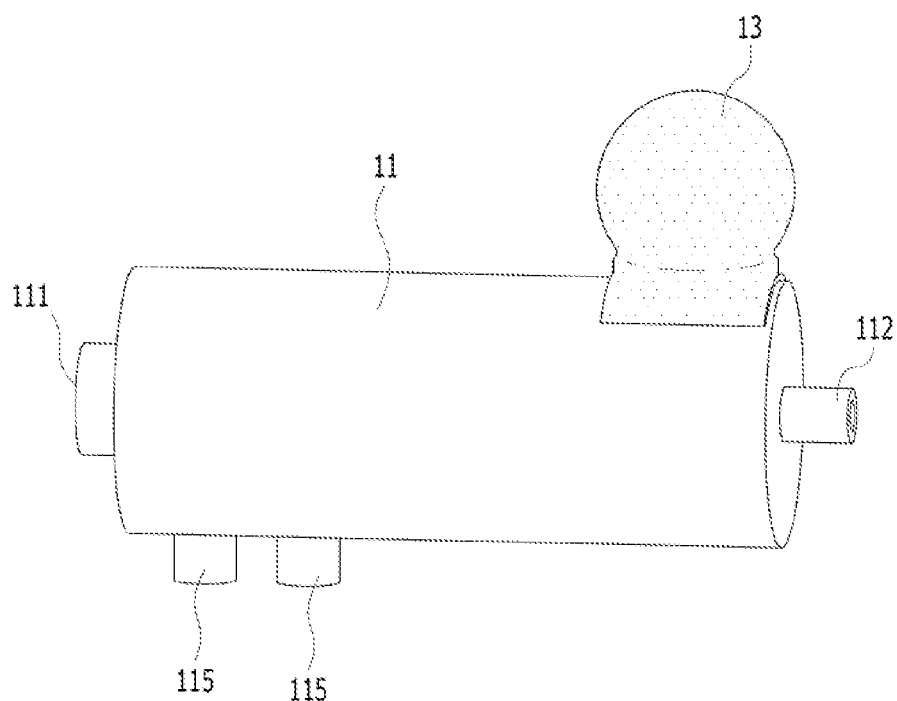
FIG. 2 is a perspective view schematically showing a tube connector for medical treatment according to a preferred embodiment of the present invention.
Figure 3:
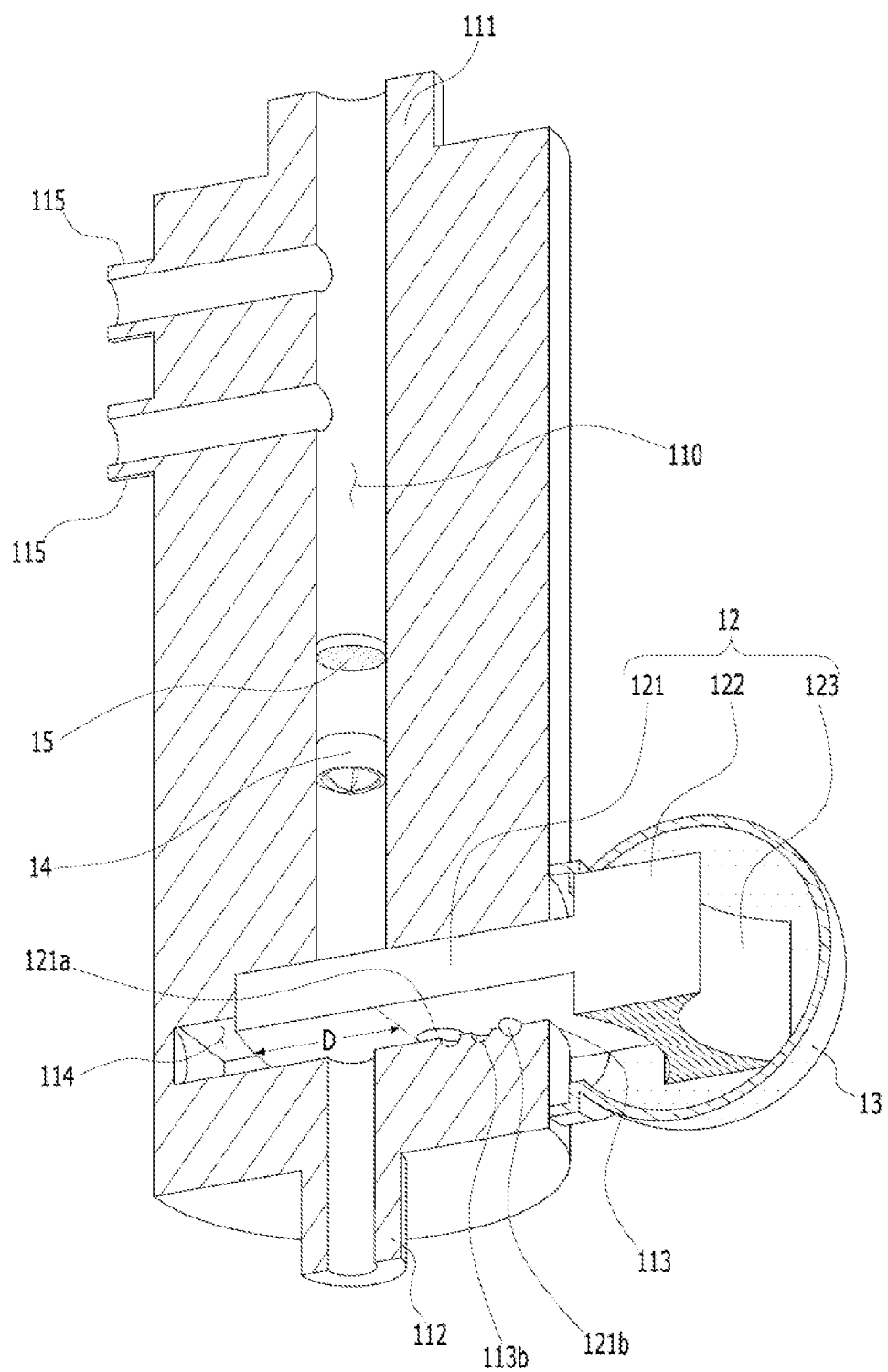
Figure 4:
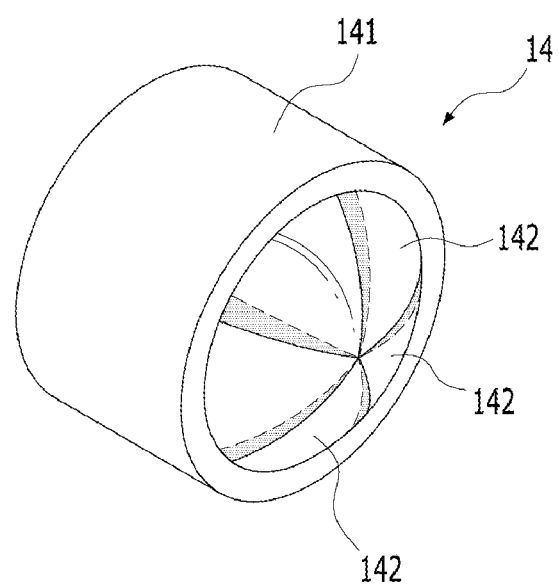
FIG. 4 is a perspective view of a check valve, which will be applied to the tube connector for medical treatment according to the present invention, when viewed from the front.

Referring to FIGS. 2 to 4, the tube connector 1 for medical treatment according to the preferred embodiment of the present invention includes a housing 11 coupled to the intravenous fluid vessel 2 and/or to the intravenous fluid supply tube 3 (3a and 3b), a push button 12 configured to open and close an internal channel 110 of the housing 11, and a balloon 13 disposed at the outer surface of the housing 11, the balloon 13 being configured to receive the upper part of the push button 12 therein.

The housing 11 is a tubular member that is coupled to the intravenous fluid vessel and/or to the intravenous fluid supply tube 3 and has the internal channel 110, which will be used as a movement path of the intravenous fluid, as described above. The housing 11 has an inflow pipe 111 integrally formed at the front end of the housing so as to fluidly communicate with the internal channel 110 and an outflow pipe 112 integrally formed at the rear end of the housing so as to fluidly communicate with the internal channel 110. Specifically, the upstream side intravenous fluid supply tube 3a may be coupled to the inflow pipe 111 of the housing 11 by insertion, and the downstream side intravenous fluid supply tube 3b may be coupled to the outflow pipe 112 of the housing 11 by insertion (see FIG. 1). Preferably, the inflow pipe 111 and the outflow pipe 112 may be disposed in a straight line.

The housing 11 has an insertion hole 113 formed from the outer surface to the internal channel 110 of the housing 11. The insertion hole 113 allows upward and downward movement of the push button 12 configured to open and close the internal channel 110. In addition, the housing 11 has a reception recess 114 formed from the inner circumferential surface of the internal channel 110 opposite the insertion hole 113 in the thickness direction thereof. The reception recess 114 is a space configured to receive the end of the push button 12 that is pushed and thus moves downwards when the internal channel 110 is closed. As shown, the insertion hole 113 and the reception recess 114 are formed in the thickness direction of the housing, which is perpendicular to the axial direction of the housing, and are arranged in a straight line.

Optionally, the housing 11 may have at least one branch pipe 115 formed so as to be adjacent to the front end thereof. The at least one branch pipe 115 is disposed so as to fluidly communicate with the internal channel 110 formed in the housing. That is, the at least one branch pipe 115 may be coupled to the intravenous fluid vessel 2 in order to supply the intravenous fluid stored in the intravenous fluid vessel to the downstream side via the internal channel 110 of the connector 1 independently of the inflow pipe.

In the present invention, the push button 12, which assists in opening and/or closing the internal channel 110 of the housing 11, is disposed in the insertion hole 113 of the housing 11 so as to be movable upwards and downwards.

Specifically, the push button 12 includes a length portion 121 having a through hole 121a formed therethrough and an extension portion 122 provided at the upper end of the length portion 121. The push button 12 may further include a push portion 123 formed at the upper end of the extension portion. The length portion 121 has a size and a shape sufficient to reciprocate in the insertion hole 113, whereas the extension portion 122 is formed so as to be larger than the insertion hole 113. That is, the downward movement of the length portion 121 is limited by a step between the length portion 121 and the extension portion 122 of the push button 12, and the insertion hole 113 is completely covered by the extension portion 122, whereby it is possible to prevent unnecessary leakage of the intravenous fluid through the insertion hole 113. In the present invention, the lower contact surface of the extension portion 122 is formed in a shape corresponding to the outer surface of the housing so as to be brought into tight contact with the outer surface of the housing 11 adjacent to the insertion hole 113. In addition, a sealing member (not shown) may be further disposed on the contact surface of the extension portion 122 that is brought into surface contact with the circumference of the insertion hole 113 of the housing 11.

As described above, the through hole 121a is formed through the length portion 121 so as to be spaced apart from the free end of the length portion 121 by a predetermined distance D. Preferably, the distance D is equal to or greater than the distance between the reception recess 114 and the through hole 121a or the distance between the reception recess and the internal channel. The fixing end of the length portion 121 is integrally coupled to the extension portion 122.

Optionally, the tub connector for medical treatment according to the present invention is configured to couple the intravenous fluid supply tubes 3a and 3b, which have different diameters, to each other such that intravenous fluid supply tubes fluidly communicate with each other. For example, the through hole 121a, which has a sectional shape that is wide at the front thereof and is narrow at the rear thereof, may be disposed between the upstream side internal channel 110, which has a large diameter, the downstream side internal channel 110, which is formed across the interior of the outflow pipe 112 and has a small diameter, in order to securely fix the downstream side intravenous fluid supply tube 3b, which is a mini volume tube, to the outflow pipe 112. To this end, a through hole having a sectional shape that is narrow at the front thereof and is wide at the rear thereof may be formed through the length portion 121 of the push button 12 (see FIGS. 5A and 5B).

In the present invention, the push portion 123, which is configured to push the push button 12 downwards, may be formed at the upper end of the extension portion 122. As shown, the push portion 123 is formed in a concave shape in order to assist seating of a finger thereon.

Particularly, in the present invention, the balloon 13 is configured such that the lower part thereof is open and the upper part thereof is formed in a dome shape. The lower part of the balloon 13 is fixed to the outer surface of the housing so as to surround the insertion hole 113 of the housing 11. Preferably, the lower part of the balloon is securely coupled to the housing such that fluid tightness is guaranteed therebetween. In addition, the balloon 13 may be made of an elastically deformable material.

As is well known by those skilled in the art, in the case in which the injection port 4 of the intravenous fluid infusion set is exactly inserted into a blood vessel or in the case in which the intravenous fluid vessel 2 is contracted by external abnormal pressure, blood and/or the injected intravenous fluid flows backwards to the intravenous fluid supply tube through the injection port (see FIG. 1). This backward flow phenomenon not only affects accurate intravenous fluid supply and management based on the prescription of a doctor but also contaminates the intravenous fluid in the intravenous fluid supply tube and/or in the intravenous fluid vessel due to mixing of the intravenous fluid and other medicines.

In the present invention, therefore, the tube connector 1 for medical treatment may include a check valve 14. In the present invention, the intravenous fluid flows only in one direction, e.g. from the connector to the injection portion, by the check valve 14, whereby foreign matter is prevented from being introduced to the upstream side of the connector.

The check valve 14 may be disposed in the housing. As shown, the check valve 14 may be disposed at the upstream side of the push button 12. However, the present invention is not limited thereto. The check valve 14 may be disposed at the downstream side of the push button 12. In addition, the check valve 14 may be further disposed in the intravenous fluid supply tube and/or in the branch pipe 115.

The check valve 14 includes a ring-shaped frame 141 disposed around the inner circumferential surface of the internal channel 110 and/or the branch pipe 115 and a plurality of segment panels 142 disposed around the ring-shaped frame 141 in a dome shape. Specifically, the plurality of segment panels 142 of the check valve 14 is formed in a curved triangular shape, as shown. The sides of the segment panels 142 overlap each other such that the plurality of segment panels 142 is disposed so as to be convex toward the downstream side. The bases of the curved triangular shaped segment panels 142 of the check valve 14 are fixed to the ring-shaped frame 141.

In addition, each of the segment panels may be made of a material that is soft, elastic, and harmless to the human body such that the segment panel can be opened by the pressure of an intravenous fluid to be supplied to the inflow pipe 111 and/or to the branch pipe 115. In particular, the plurality of segment panels 142 is disposed in the circumferential direction of the frame 141 such that one side of one segment and the other side of another segment overlap each other. In this disposition structure, a gap is provided between the sides of the segment panels disposed so as to overlap each other by the pressure of an intravenous fluid to be supplied to the inflow pipe and/or to the branch pipe, as described above, and the intravenous fluid is transferred to the downstream side through this gap, whereas, in the case in which the pressure of an intravenous fluid to be supplied to the inflow pipe and/or to the branch pipe decreases or a backward flow occurs, the segment panels 142 disposed adjacent to each other are brought into tight contact with each other by the restoring force of the segment panels, whereby the backward flow is prevented. In addition, the sides of the segment panels disposed adjacent to each other are disposed so as to overlap each other, whereby the supporting force of the segment panels is increased and thus the segment panels are maintained in a dome shape.

Optionally, in the present invention, a filter 15 is disposed in the connector 1 in order to prevent foreign matter from being discharged to the injection port 4 together with the intravenous fluid through the downstream side intravenous fluid supply tube 3b. The filter 15 may be disposed at the upstream side of the check valve 14 in order to filter the intravenous fluid before the intravenous fluid is transferred to the downstream side. However, the present invention is not limited thereto. The filter 15 may be integrally provided at the front end of the check valve 14, specifically the ring-shaped frame 141.

Figure 5A:
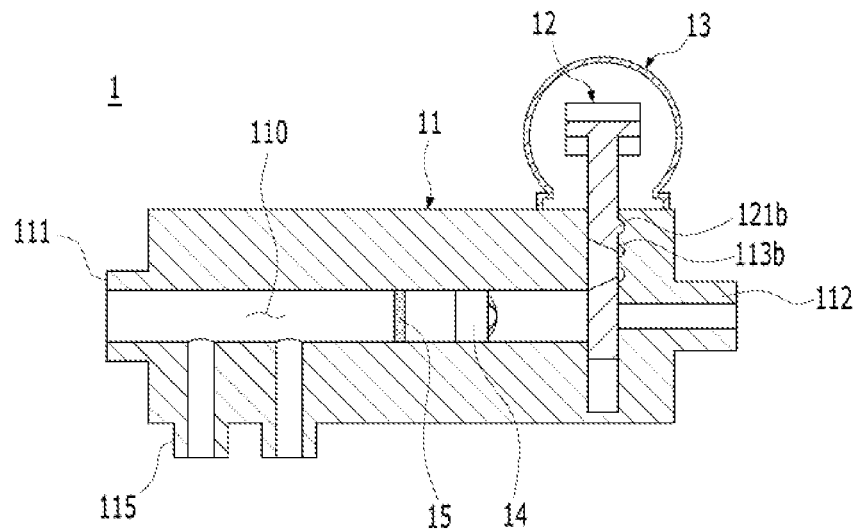
FIG. 5A is a view showing the closed state of the tube connector for medical treatment shown in FIG. 2.
Figure 5B:
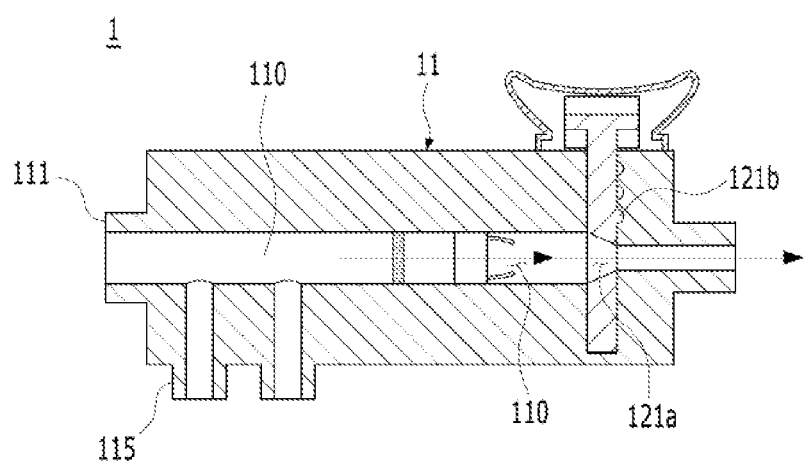
FIG. 5B is a view showing the open state of the tube connector for medical treatment shown in FIG. 2.

FIG. 5A and FIG. 5B are the view showing the state in which the tube connector for medical treatment according to the preferred embodiment of the present invention is used.

The tube connector 1 for medical treatment according to the present invention may restrict the transfer of an intravenous fluid that is supplied from the inflow pipe 111 and/or to the at least one branch pipe 115 to the downstream side. As shown in FIG. 5A, in the tube connector 1 for medical treatment according to the present invention, the internal channel 110 is blocked by the length portion of the push button 12, which is disposed across the internal channel, whereby control may be performed such that an intravenous fluid supplied from the upstream side of the connector is not guided to the downstream side. That is, no external force is applied to the balloon, whereby the balloon is maintained in a convex dome shape, and therefore it is possible to sufficiently confirm that the internal channel of the connector is blocked with the naked eye. Preferably, the housing 11, the push button 12, or the balloon 13 may be made of a transparent material such that the interior of the connector is easily visible.

Referring to FIG. 5B, when a user pushes the balloon 13, the push button 12 is pushed toward the reception recess, whereby the through hole 121a of the length portion is aligned with the internal channel 110 in a line so as to fluidly communicate therewith in order to allow the intravenous fluid to move to the downstream side of the connector in a direction indicated by an arrow. It is possible for the user to confirm the pushed balloon with the naked eye and thus to recognize the state in which the internal channel of the connector is open.

Optionally, the push button 12 may have a coupling protrusion 121b formed on the outer surface of the length portion 121 and at least one coupling recess 133b formed in the inner surface of the insertion hole 113 so as to correspond to the coupling protrusion. The coupling protrusion 121b may be disposed between the through hole 121a and the extension portion 122. However, the present invention is not limited thereto. The coupling protrusion may be disposed between the through hole 121a and the free end of the length portion. Correspondingly, the at least one coupling recess may be provided in the inner surface of the reception recess 114. The at least one coupling recess 113b may be aligned in the upward-downward movement direction of the push button 12 disposed so as to be perpendicular to the internal channel. When the intravenous fluid is moved through the connector, the coupling protrusion 121b of the push button 12 is received in the lowermost coupling recess 113b, and therefore the open state of the connector may be maintained unless additional external force is applied to the push button. In the present invention, the coupling protrusion 121b is inserted into any one of the coupling recesses 113b, formed in a direction perpendicular to the internal channel, by external force. In this case, it is possible to control the amount of an intravenous fluid to be supplied by adjusting the size of the overlapping area between the inner channel and the through hole through a process of changing the insertion depth of the push button.

As described above, the user may push the side surface of the pushed balloon or may forcibly move the push portion 123 of the push button upwards such that the push button 12 is moved upwards and thus the internal channel is blocked by the length portion, as shown in FIG. 5A. At this time, the coupling protrusion 121b of the push button 12 is received in the uppermost coupling recess 113b, whereby the downward movement of the push button is not allowed. The elastically deformable balloon 13 may be restored to the original shape thereof, i.e. the dome shape. In addition, airtightness is achieved between the balloon and the housing. Even in the case in which an intravenous fluid leaks through the insertion hole 113, therefore, the intravenous fluid is collected in a space defined in the balloon, whereby the intravenous fluid is prevented from being discharged to the outside.

Optionally, the outer surface of the push button 12, specifically the outer surface of the extension portion 122, may be made of an elastic material. In this case, it is possible to guide the upward movement of the push button by pushing the end of the extension portion 122, which has elastically restoring force, and to minimize damage to the balloon, which has a predetermined volume therein, when the push button comes into contact with the balloon.

Figure 6:
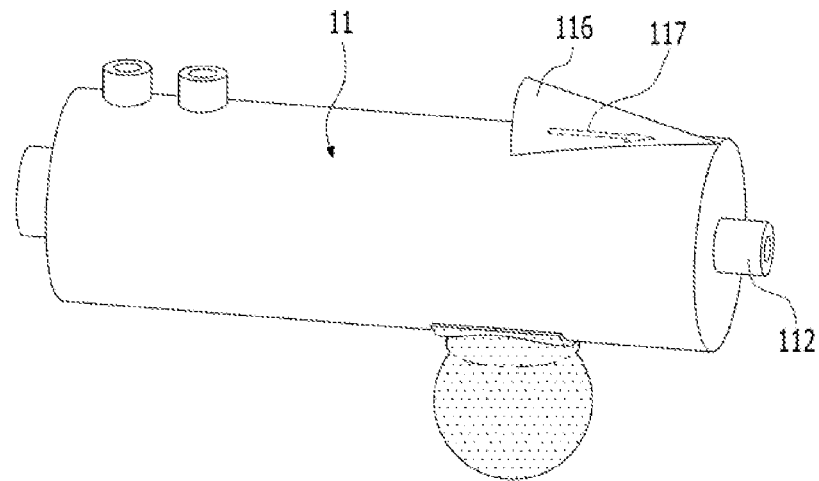
FIG. 6 is a perspective view schematically showing a tube connector for medical treatment according to another embodiment of the present invention.

FIG. 6 is a perspective view schematically showing a tube connector for medical treatment according to another embodiment of the present invention. The tube connector for medical treatment shown in FIG. 6, which is a modification of the tube connector for medical treatment shown in FIG. 2, is very similar in construction to the tube connector for medical treatment shown in FIG. 2 except for the external shape of the housing. Hereinafter, therefore, a description of the same or similar elements will be omitted for clear understanding of the present invention.

In the tube connector for medical treatment according to the other embodiment of the present invention, it is possible to confirm the open or closed state of the internal channel based on the pushed state of the balloon, as previously described. Also, in the tube connector for medical treatment according to the other embodiment of the present invention, a conical direction indicator 116 having a direction set to the downstream side is formed on the downstream side outer surface of the housing 11 adjacent to the outflow pipe 112 so as to protrude therefrom in order to indicate the movement direction of an intravenous fluid.

Preferably, in the present invention, a light-emitting layer 117 may be disposed between the outer surface of the housing and the direction indicator 116 such that the movement direction of the intravenous fluid is easily recognized even at night. The light-emitting layer 117 may be made of a luminous material or a fluorescent material capable of providing light to the surroundings even in the dark.

Figure 7:
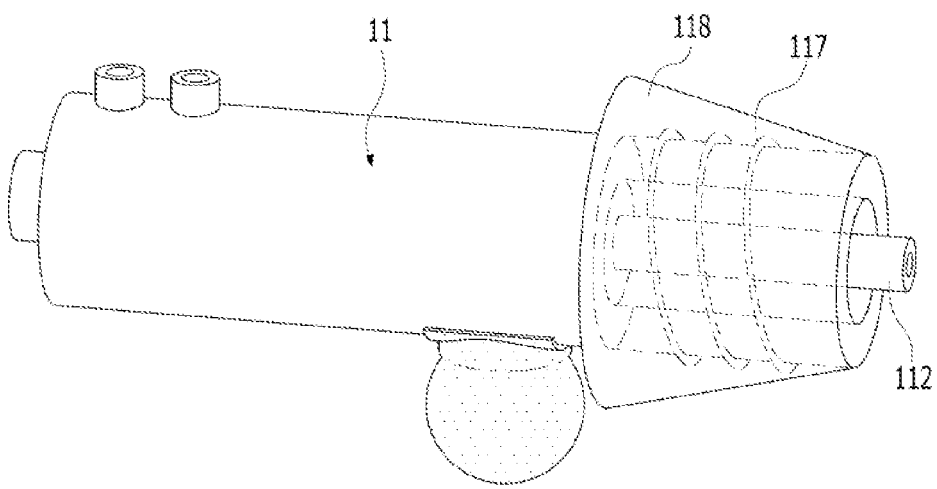
FIG. 7 is an exploded perspective view schematically showing a tube connector for medical treatment according to a further embodiment of the present invention.

FIG. 7 is a view schematically showing a tube connector for medical treatment according to a further embodiment of the present invention. The tube connector for medical treatment according to the further embodiment of the present invention includes a hollow direction indicator 118 having a truncated conical shape, in other words, a tubular direction indicator having a truncated conical shape, provided on the downstream side outer surface of the housing, the direction indicator being configured to indicate the movement direction of an intravenous fluid.

The hollow direction indicator 118 having the truncated conical shape extends from the downstream side outer surface of the housing in the longitudinal direction of the housing, and may be arranged in a dual pipe shape in which the direction indicator is disposed so as to be spaced apart from the outer circumferential surface of the outflow pipe 112. In this case, the downstream side intravenous fluid supply tube 3b shown in FIG. 1 may be interposed between the outflow pipe 112 and the direction indicator 118.

In the further embodiment of the present invention, a ring-shaped or spiral light-emitting layer 117 may be disposed around the inner circumferential surface of the hollow direction indicator 118 having the truncated conical shape or in the direction indicator 118.

In addition, the present invention is not limited as to the shapes of the direction indicator 118 shown in FIGS. 6 and 7.

As is apparent from the above description, the present invention provides a tube connector that assists in supplying an intravenous fluid that is supplied from an inflow pipe and/or at least one branch pipe into the body of a patient via an intravenous fluid supply tube.

As previously described, according to the present invention, it is possible to supply an intravenous fluid that is supplied from the inflow pipe and/or the at least one branch pipe to the downstream side individually or after being mixed.

In addition, according to the present invention, the tube connector is configured to have a simple structure capable of rapidly and easily opening and closing an internal channel of the connector.

According to the present invention, a check valve is mounted in the connector, whereby it is possible to move an intravenous fluid only in one direction, i.e. from the upstream side to the downstream side.

In addition, according to the present invention, the tube connector is designed such that a filter and the check valve are disposed in that order, whereby only an intravenous fluid from which foreign matter has been removed is moved to the downstream side.

Although the present invention has been described in detail with reference to the embodiments, the embodiments are provided to describe the present invention in detail, the tube connector for medical treatment according to the present invention is not limited thereto, and those skilled in the art will appreciate that various modifications, additions and substitutions are possible, without departing from the scope and spirit of the invention as disclosed in the accompanying claims.

Simple changes and modifications of the present invention are to be appreciated as being included in the scope and spirit of the invention, and the protection scope of the present invention will be defined by the accompanying claims.

What is claimed is:

1. A tube connector for medical treatment comprising:
    a housing comprising an internal channel configured to define a movement path of an intravenous fluid, an inflow pipe formed at a front end of the housing so as to fluidly communicate with the internal channel, an outflow pipe disposed at a rear end of the housing so as to fluidly communicate with the internal channel, an insertion hole formed from an outer surface of the rear end of the housing to the internal channel, a reception recess formed from an inner circumferential surface of the internal channel in a thickness direction of the housing so as to be opposite the insertion hole, and at least one branch pipe disposed at an outer surface of the front end of the housing so as to fluidly communicate with the internal channel;
    a push button comprising a length portion having a through hole formed therethrough which has a sectional shape that is wide at a front thereof and is narrow at a rear thereof and an extension portion located at an upper end of the length portion so as to be disposed at an outer surface of the housing, the push button being disposed in the insertion hole so as to be movable upwards and downwards; and
    an elastically deformable dome-shaped balloon configured to surround the insertion hole of the housing, a lower part of the balloon being open, wherein
    the internal channel of the housing is opened and closed through upward and downward movement of the push button.

2. The tube connector according to claim 1, wherein
    a check valve is disposed in the internal channel or the branch pipe of the housing, and
    a filter is disposed in the internal channel or the branch pipe of the housing.

3. The tube connector according to claim 2, wherein
    the check valve comprises:
    a ring-shaped frame disposed around an inner circumferential surface of the internal channel or the branch pipe; and
    a plurality of segment panels disposed around the ring-shaped frame in a dome shape,
    the plurality of segment panels being formed in a curved triangular shape that is convex toward a downstream side, sides of the segment panels being disposed so as to overlap each other.

4. The tube connector according to claim 1, wherein
    at least one coupling recess is provided in an inner surface of the insertion hole of the housing in an upward-downward movement direction of the push button, and
    a coupling protrusion is provided on an outer surface of the length portion of the push button.

5. The tube connector according to claim 1, wherein a direction indicator configured to indicate a movement direction of the intravenous fluid is provided at a downstream side outer surface of the housing adjacent to the outflow pipe.

* * * * *